Figure 1:
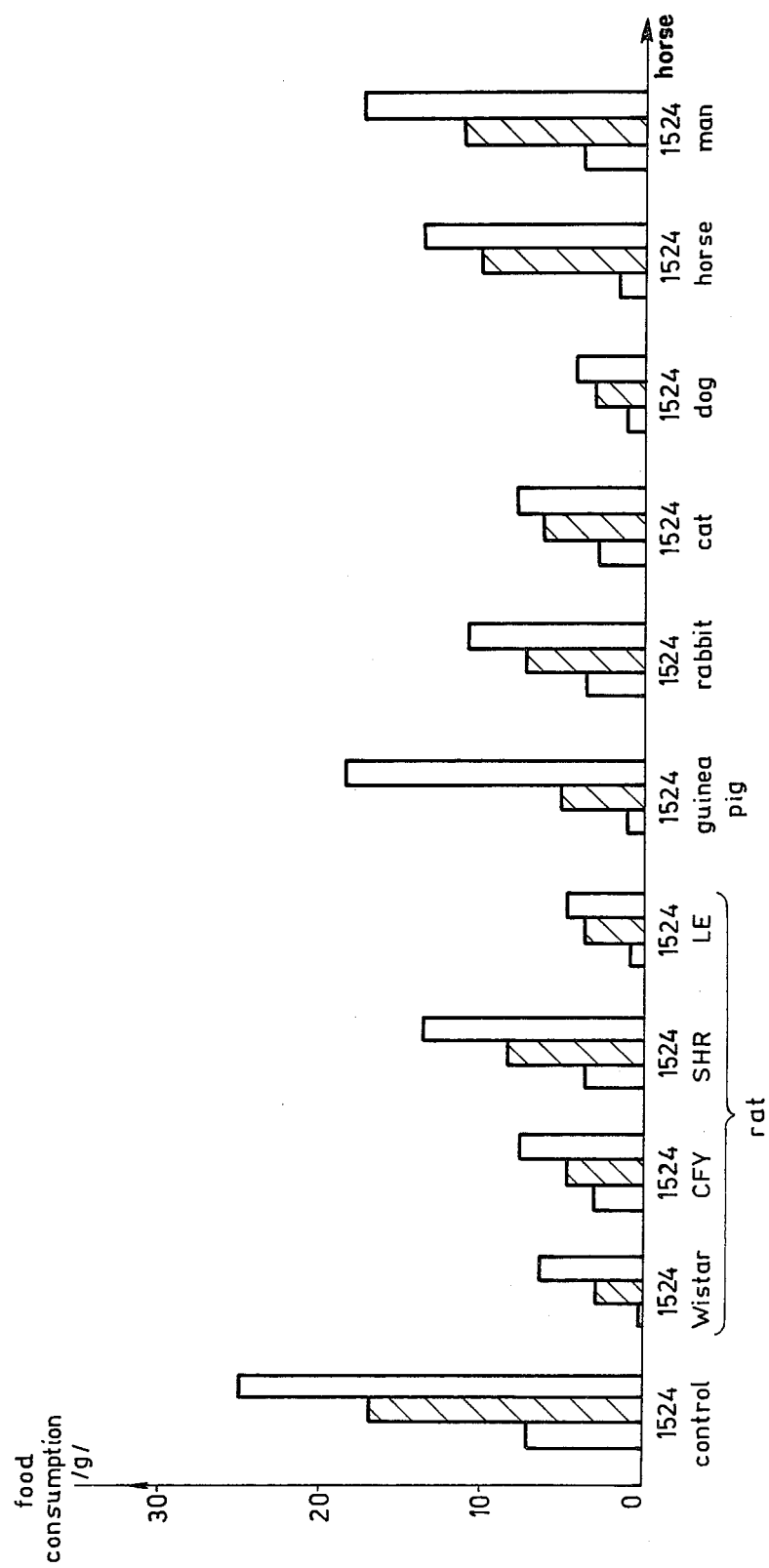

United States Patent [19]

Knoll et al.

[11] 4,294,825

[45] Oct. 13, 1981

[54] PROCESS FOR THE PRODUCTION OF AN ANDREXOGENIC SUBSTANCE HAVING SPECIFIC EFFECT ON THE CENTRAL REGULATION OF FOOD INTAKE

[75] Inventors: Jozsef Knoll; Huba Kalasz; Berta Knoll, all of Budapest; Janos Nagy, Szentendre, all of Hungary

[73] Assignee: Richter Gedeon Vegyészeti Gyár RT, Budapest, Hungary

[21] Appl. No.: 68,766

[22] Filed: Aug. 23, 1979

[30] Foreign Application Priority Data

Aug. 29, 1978 [HU] Hungary ................................ RI 683

[51] Int. Cl.³ .......................... A23J 1/06; A23K 1/04; C07G 7/00

[52] U.S. Cl. ................................ 424/101; 260/112 B; 424/177

[58] Field of Search ..................... 424/101; 260/112 B

[56]  References Cited

PUBLICATIONS

Physiology & Behavior, vol. 23, pp. 497–502, Sep. 1979, Knoll.

Chem. Abstracts, vol. 91, 208025y, Knoll.

Primary Examiner—Howard E. Schain
Attorney, Agent, or Firm—Karl F. Ross

[57]  ABSTRACT

Described is the method of preparing satietin, a peptide separated from plasma or serum and possessing the effect of inhibiting food intake. Also described is the product satietin.

5 Claims, 2 Drawing Figures

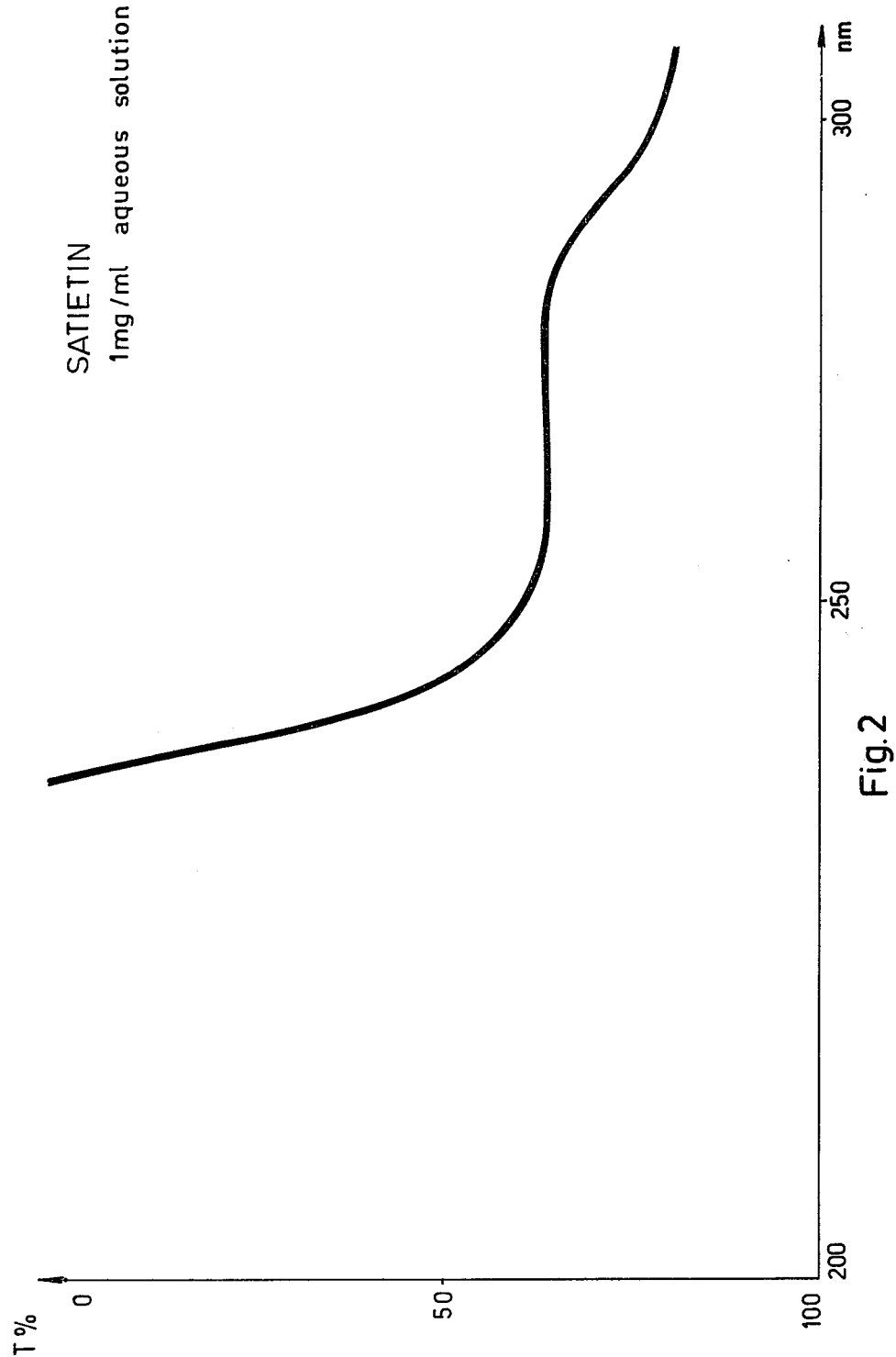

PROCESS FOR THE PRODUCTION OF AN ANDREXOGENIC SUBSTANCE HAVING SPECIFIC EFFECT ON THE CENTRAL REGULATION OF FOOD INTAKE

The subject of the invention is the process for the production of a substance, named satietin, which has specific effects on the central regulation of food intake. According to the invention the specific effects of the substance are due to the selective inhibition of the food intake, at the same time the substance has no other effect on the central nervous sytem; neither a depressive effect nor an effect inhibiting motor activity can be observed.

Among the drugs and medicines, mainly amphetamine-like substances are applied at present for reducing appetite; the anorexogenic effect is not specific at all, these substances also have undesired central and peripheral sympathomimetic or serotonergic effects. Their further disadvantage is the development of tolerance to the anorexogenic effect which interferes considerably with their effectiveness. Cholecystokinin, a putative satiety signal in modulating food intake, is only of theoretical interest as it has direct effects on the gastrointestinal tract and it is an anorexogenic of low potency.

So there is no exogenous or endogenous anorexogenic substance at our disposal which would affect selectively the central regulation of food intake without undesirable side-effects, and which would have a potency desired for therapy.

That is why our finding that a hitherto unknown substance can be separated from human and animal plasma which has a selective and extremely strong effect as a satiety signal, inhibiting food intake in rats deprived of food for 96 hours. The substance also has great importance from the point of view of medicinal treatment of any type of hyperphagia and concomitant obesity. This new substance which can be separated by membrane filtration and gel chromatographic fractionation from human and animal plasma, seems to have a molecular weight above 60 000. Aminoacids and carbohydrates can be found in its hydrolysate, the aminoacids include asparagine, leucine, glutamic acid, lysine in the greatest quantity; threonine, glycine, cysteine, tyrosine, phenylalanine, arginine, histidine, proline, serine, alanine, valine, methionine, isoleucine and tryptophan can be found in smaller quantity; as for carbohydrates, glucose, galactose, mannose, rhamnose and arabinose can be found besides other reducing substances in smaller quantity. The identification of its chemical structure is detailed hereinafter; the examinations of its molecular structure is in progress.

This new glycoprotein, named satietin, with a highly selective satiety effect is produced in the following way: human or animal serum is filtered through a membrane filter letting substances under 50,000 molecular weight pass through; the filtrate is dried, dissolved in water, and separated by gel chromatography on a gel with a void volume under 50 000, by eluting with salt water; the fractions having biological activity are collected, dried dissolved in water and purified by further chromatography on a gel with a void volume under 50 000; the biologically active fractions are then freeze-dried.

The first step of the process of invention is the ultrafiltration of human and animal serum through a filter which lets the substances with a molecular weight of less than 50,000 pass through. Amicon UM 10 or other membranes of the Amicon type of Sartorius membrane having similar pore size can be used. According to our experiences Amicon UM 05, UM 2, DM 5, UM 10, PM 10, UM 20, PM 30 and XM 30, or Sartorius 121 33, 121 34 and 121 36 membranes proved to be suitable for this purpose.

Membrane filtration was carried out under pressure (preferably 3 atm) with constant stirring. The serum is divided into two fractions by membrane filtration: the molecules greater than the pore size of the membrane are separated from the smaller ones. During this process the substance of the invention, satietin surprisingly appears in total quantity in the fraction containing substances of low molecular weight (under 10 000 daltons), in spite of the fact that the filtration is carried out with a membrane filter which lets substances with a molecular weight of under 50,00 pass through, and satietin-as mentioned above-is supposed to have a molecular weight between 60 000 and 100 000 daltons. This atypical behavior of the new substance is advantageous from the point of view of the process of the invention, because it essentially facilitates the separation of the new substance from other substances being similarly, large molecules. Thus the new substance can be found in the filtrate of the membrane filtration concentrated ten- and twenty-fold as compared to the original dry substance content of the serum, together with other substances having a much smaller molecular weight.

The second step of the process is the solution in distilled water of the dry residue obtained by the evaporation of the filtrate, then it is chromatographied on a gel having a void volume under 50 000. First of all Sephadex G-15, G-10, G-25, G-50, G-75 and Bio-Gel P-2, P-4, P-6, P-10, P-30 or P-60 gels can be used with good results. The column is eluted with physiological sodium-chloride solution or with other solutions containing 0.1% of sodium chloride at least or another salt capable of maintaining a neutral pH value. During elution the new substance appears at or near to the void volume (it is known that in the case of gel chromatographic separations the "void volume" of the gel is an important characteristic: all the molecules which are near or above the upper verge of the selective separational volume of the gel, in the case of Sephadex G-15 gel it is 1500, elute near to the void volume, at the eluting volume which means 25–35% of the volume of the column), while the concomitant substances with smaller molecular weight being present even after membrane filtration appear later at greater elution volume, separated into more peaks. Biologically active fractions are collected and freeze dried.

In the third step of the isolation this dry residue containing the multiconcentrated effective substance is again fractionated by gel-chromatography. As a result of this step a pure, effective product, suitable for therapeutic purposes can be obtained by elution with distilled water. This second chromatographic purification is also carried out on a column with a void volume under 50 000. The dry residue obtained from the first fractionation is dissolved in distilled water of the minimally necessary quantity and separated on a column of Bio-Gel P-30 gel and eluted with distilled water. The biologically active fractions are collected and lyophilized.

Thus a pure, homogenous product is obtained, but if the electrophoretic examination of the product would show the presence of some contaminations, the effective substance can be further purified with chromatography on a diethyl-amino-ethyl-cellulose column. The substance is given to the diethyl-amino-ethyl-cellulose column in distilled water solution, the column is washed with distilled water, then it is eluted with 0.1 N phosphate-buffer-solution (pH=6.5)–0.1 N phosphate-buffer-solution (pH=6.5) containing 5% NaCl solution gradient. The pure and biologically active substance is eluted from the column with 0.1 N phosphate buffer solution (pH=6.5)+0.5–0.7% NaCl, the elute fraction containing the pure substance is lyophilized, then the substance is desalted from the inorganic acids on Bio-Gel P-30 gel and eluted with distilled water.

The homogeneity of the pure substance can be examined with electrophoresis on polyacrylamide gel containing 15% acryl-amide, with a buffer solution of pH=4.5, at 100 V and at a current of 4 mA for each tube.

The new substance, satietin, is a white, cotton-like substance, its chemical analysis shows that it is a glycopeptide, after its acidic hydrolysis amino acids and carbohydrates can be detected. The results of our examinations to determine the chemical composition and structure of satietin obtained from human serum are the following:

The aminoacidic and saccharidic composition of the product by hydrolysis

| Amino acids: | |
|---|---|
| lysine | 6.0% |
| histidine | 1.6% |
| arginine | 3.0% |
| | 10.6% |
| carry-forward: | 10.6% |
| cystein | 2.3% |
| asparagine acid | 7.0% |
| threonine | 3.1% |
| glutaminic acide | 9.6% |
| serine | 1.7% |
| proline | 2.2% |
| glycine | 1.2% |
| alanine | 3.8% |
| valine | 3.6% |
| methionine | 1.3% |
| isoleucine | 1.0% |
| leucine | 6.0% |
| tyrosine | 1.8% |
| phenyl-alanine | 3.5% |
| tryptophan | 1.9% |
| total amino acid content: | 60.6% w/w |

In the product there is 13% reducing substances mainly carbohydrates

| glucose | 2.8% |
|---|---|
| galactose | 2.9% |
| mannose | 2.0% |
| rhamnose | 1.9% |
| arabinose | 1.1% |
| total carbohydrate content: | 10.7% w/w |

Water content:
The product contains also physically bound water in 10%.

N-terminal sequence analysis:
During further examination of the product we applied the usual methods of N-terminal residue analysis—with dansyl-derivatives and cleavage with aminopeptidase M enzyme—and no residue could be obtained, which means the presence of masked N-terminal residue.

Enzymatic hydrolysis with trypsin:
Satietin practically can not be digested with trypsin during 2 hours in pH=8.3 ammonium-hydrogencarbonate buffer; the color intensity of the appearing peptide-zones is weak.

The effect of carboxymethylation on the structure:
Satietin-which seems to be a homogeneous substance with a molecular weight of about 68 000 during polyacrylamide gel-electrophoresis, after the bonding of the SH-groups with bromo-acetic-acid, seems to have 4 components in the electrophoretic picture obtained by electrophoresis with sodium-dodectil-sulphate: the component having a molecular weight of about 68 000 is present, but there is another one with 18 000 and two, similarly mobile, but well-differentiated components with molecular weight of about 28 000.

The effect of carboxymethylation on the acitivity:
Satietin looses its biological activity if carboxymethylated with bromo-acetic-acid.

UV-spectrum:
The ultraviolet absorption spectrum of satietin does not show absorption-maximum, a "plateau" appears at about 275–280 which may be a characteristic of a protein-peptide. The absorption spectrum is demonstrated in FIG. 2.

Molecular weight:
The interesting characteristic of satietin is its above mentioned particular behavior during the different measurements of the molecular weight:
(1) During ultrafiltration on the membrane it seems to have a molecular weight under 10 000.
(2) Upon gel chromatographic examination it seems to have a molecular weight above 40 000, between 60 000 and 100 000.
(3) Upon polyacrylamide gel-electrophoresis it goes together with molecules having a molecular weight between 65 000 and 68 000.
(4) Upon ultracentrifugation it appears to have a molecular weight under 10 000.

The new substance, which can be produced according to the process described in the invention, need not be obtained from human serum only, but the serum of different animals can be also used. Though the substances obtained from the serum of different mammals: cattle, dog, cat, horse, guinea-pig, rabbit, different strains of rats (Wistar, CFY, SHR, Long Evans) with the same method—presented difference in potency, the specificity of the effect, i.e. the selective inhibition of food intake, is the same for every product.

The effect of the product on the food intake was examined on female CFY rats weighing 200–240 g. The animals have been deprived of food for 96 hours before the experiments, water was supplied ad lib. Considering the agressivity resulting from starving, the animals were put in individual cages, individually. Each animal was given i.v. 10 mg/kg dose of satietin dissolved in 0.5 ml of physiological salt solution. Animals of the control group were injected only with 0.5 ml physiological salt solution i.v., without the substance in it. One hour after the treatment the animals were offered food: the usual chow pellet containing albumine, fat, carbohydrate and vitamins, in unrestricted quantity. The food consumption was measured 1.5 and 24 hours after giving the food (or 2, 6, 25 hours after treatment). The results are presented in FIG. 1. The empty columns represent the amount of the food eaten in 1 hour; the striped one that of 5 hours, the shadowed one that of 24 hours, under the columns the animals are indicated from the serum of which the satietin sample was extracted. The results presented prove the extreme effectiveness of the product of the invention: its effect surpasses that of the hitherto known substances with similar effect, at the same time cholecystokinin and arentenin which is produced from duodenum extract described by Ugolev et al. have no effect at all on animals deprived of food for 96 hours. The fact that the new substance has a total effect even in this case proves its unique high activity.

To prove the specific and selective effect of the new substance, it was examined from the point of view of side effects observed on substances with similar effect (amphetamine-like substances). On the modified jumping test—which is the method for examining the central depressive effect [Knoll, J. and Knoll, B., Arch.int.-Pharmacodyn. 148, 200–217, (1964)] the new substance did not influence avoidance behavior even in a dose which was double that of inhibiting food intake. In the test carried out with the motimeter [Knoll, J. Arch.int. Pharmacodyn. 130, 141–154 (1961)] even the great i.v. doses of the new substance had not any effect of inhibiting or increasing motility. It is known, that substances with depressive effect strongly influence the conditioned reflexes, that is why similar experiments were carried out with the new substance on rats in the jumping test [Knoll, J. and Knoll, B. Arzneimittel-Forsch. 8, 330–333, (1958)] which is suitable for examining conditioned avoidance behavior. Satietin proved to be ineffective in this respect, too. Considering the fact that cholecystokinin has a characteristic contracting effect on the longitudinal muscle of the quinea pig ileum [Knoll, et al. Pharmacology, 12, 283–289, (1974)], the new substance was examined in this respect, too, on this isolated organ, and it proved to be ineffective compared to cholecystokinin. All these experiments prove the advantageous characteristics of satietin, which can be summarized as follows:

a. satietin is an endogenous substance of natural origin;
b. it does not show considerable toxicity,
c. its effect is selective, inhibiting the center of food consumption by acting on the central regulation of food intake,
d. its activity differs from that of other anorexigenic substances being devoid of depressant or stimulating effects,
e. it is very potent, as it is capable of inhibiting food intake in rats deprived of food for 96 hours,
f. its effect is dose-dependent. Maximum inhibition of food intake was reached with 200–300 μg/rat at intracerebroventricular administration,
g. the peak effect is reached in five hours after the intracerebroventricular injection of satietin and the effect is long lasting, it continues for 24 hours,
h. the effect is reversible.

The practical execution of the process of the invention is demonstrated by the following example:

1.00 l human serum is ultrafiltered through Amicon UM 10 membrane. 700 ml of filtrate is obtained, it is freeze dried, and the residue is dissolved in 30 ml distilled water. The solution is separated on a Sephadex G-15 column (diameter 5 cm, length 90 cm) eluted with 0.9% NaCl aqueous solution; fractions are collected, 10 ml each. The fractions between 50 and 60, (between 500 and 600 ml) were found to be biologically active. These fractions are collected, freeze dried and dissolved in 10 ml of distilled water. The solution is separated on a Bio-gel P-30 gel column with the dimensions of 2.5×90 cm, is eluted with distilled water. Fractions of 10 ml are collected; the fractions between 11–15 prove to be active biologically. These fractions are collected and lyophilized. Depending on the quality of the original serum, 20.0–24.0 mg dry product is obtained, which is snow-white, cotton-like, homogenous and pure substance suitable for therapeutical usage.

We claim:

1. A process for the preparation of an endogenous anorexogenic substance having a satiety effect on the central regulation of food intake which comprises the steps of:
   (a) membrane filtering mammalian serum or plasma to separate out materials having a molecular weight of up to 50,000 as a filtrate;
   (b) drying the filtrate;
   (c) dissolving the filtrate dried during step (b) in water;
   (d) chromatografically fractioning on a gel with a void volume under 50,000 the filtrate dissolved during step (c) with a 'neutral', aqueous, eluting salt solution containing at least 0.1% of the salt to obtain a fraction with high anorexogenic activity;
   (e) drying the fraction with high anorexogenic activity;
   (f) dissolving the fraction with high anorexogenic activity in water;
   (g) subjecting the fraction with high anorexogenic activity to a second chromatographic fractioning on a gel with a void volume under 50,000 with distilled water to obtain a second fraction of higher anorexogenic activity; and
   (h) lyophilizing the second fraction of higher anorexogenic activity.

2. The process defined in claim 1, step (d), wherein the salt is sodium chloride.

3. The process defined in claim 1 wherein following step (g) the second fraction of higher anorexogenic activity is subjected to a third gel chromatographic fractioning.

4. The product produced according to the process of claim 1.

5. An anorexogenic method of treatment which comprises the step of administering to a mammal an anorexogenically effective amount of the product obtained according to the process of claim 1.

* * * * *